April 13, 1937. J. A. ARMSTRONG Plant Pat. 244
ROSE
Filed Nov. 4, 1936
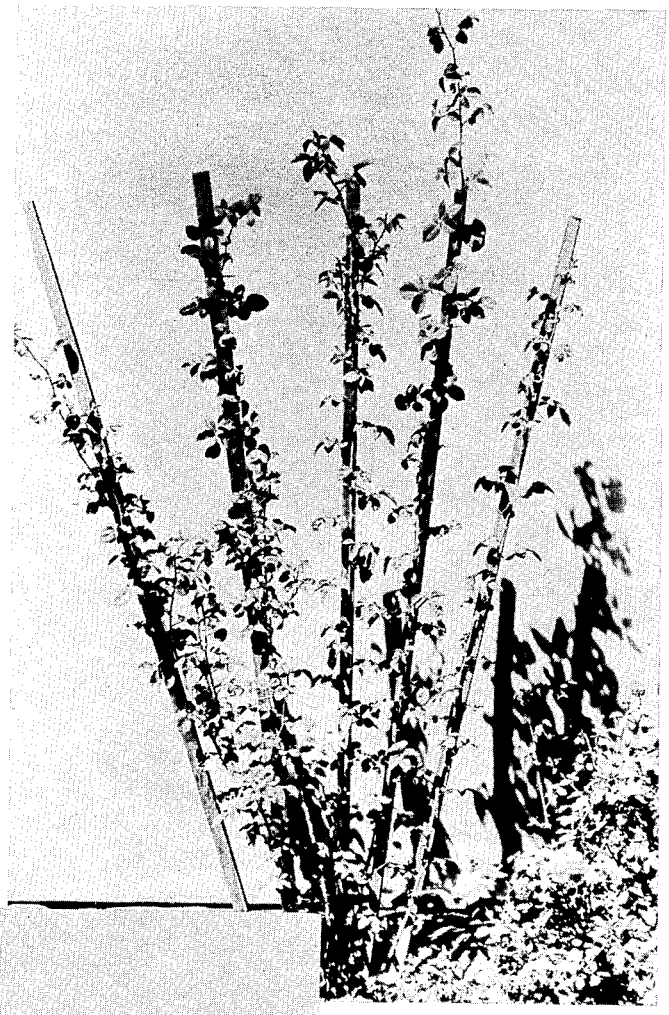
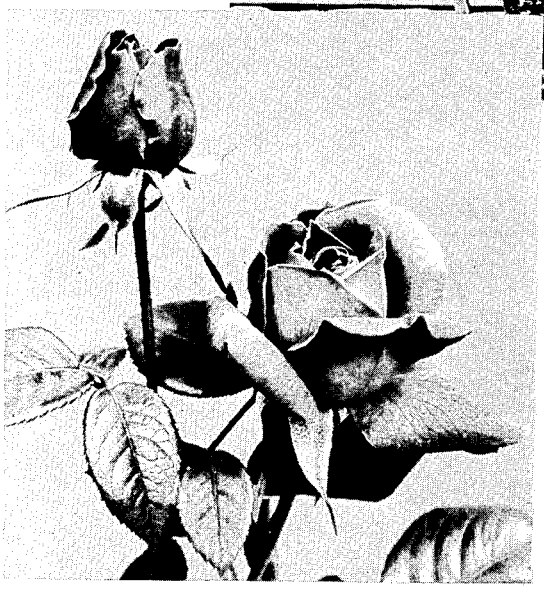
INVENTOR
John A. Armstrong
By Orville M. Kile
PLANT PATENT AGENT Patented Apr. 13, 1937

Plant Pat. 244

UNITED STATES PATENT OFFICE

244

ROSE

John A. Armstrong, Ontario, Calif., assignor to Armstrong Nurseries, Ontario, Calif.

Application November 4, 1936, Serial No. 109,174

1 Claim. (Cl. 47—61)

My invention relates to a new and distinct variety of climbing rose, the distinctive feature being a vigorous climbing habit. It originated as a sport of the rose Hinrich Gaede and closely resembles that rose except for its growing and blooming habits. It sends up stout, vigorous canes from six to ten or more feet in length as distinguished from the bush Hinrich Gaede which seldom reaches a height of more than four feet.

Another growing habit which distinguishes this variety from the bush Hinrich Gaede is the production of its largest burst of bloom in the spring, whereas the bush Hinrich Gaede blooms throughout the summer.

Because of the climbing habit and the consequent size of the plant, this new variety has more flowers appearing at once during the main blooming season in the spring than has the bush variety.

The illustration shows the climbing growth of the new variety as compared with the bush variety shown at its base; also a view of opening flowers, stems and foliage.

Following is a more detailed description of the new variety which is also a description of the bush Hinrich Gaede, except as to growth and blooming habits.

*The plant*

*Foliage.*—Bright green; large and abundant; of excellent texture; sharply serrated edges; glossy.

*Sepals.*—Short; wide; non-foliaceous.

*Growth.*—Vigorous climber, attaining a height of more than ten feet.

*Blooming habit.*—Has its largest burst of bloom in the spring with intermittent blooming throughout the summer thereafter.

*Disease resistance.*—Very healthy.

*The flower*

Bud: Particularly beautiful.

*Shape.*—Long, slender, at first, becoming ovoid as it opens.

*Size.*—Medium.

*Color.*—Coppery orange.

*Peduncle.*—Covered with numerous hair-like spines.

Bloom:

*Size.*—Medium; 25 to 30 petals.

*Form.*—Pointed, later opening into cup shape.

*Color.*—Rather uniform brilliant shade of orange-scarlet or coppery orange, same as Hinrich Gaede.

*Veining.*—Very prominent on outer petals.

*Fragrance.*—Honey-sweet fragrance.

Having thus disclosed my invention, I claim:

The new variety of rose plant herein described and illustrated, characterized particularly by its vigorous climbing habit, and its habit of producing most of its bloom in the spring but blooming intermittently throughout the season thereafter, rather than continuously as is done by the bush Hinrich Gaede.

JOHN A. ARMSTRONG.